US008996315B2

(12) United States Patent
Guo et al.

(10) Patent No.: US 8,996,315 B2
(45) Date of Patent: Mar. 31, 2015

(54) METHOD AND SYSTEM OF DETERMINING A VALUE INDICATIVE OF GAS SATURATION OF A FORMATION

(75) Inventors: Weijun Guo, Houston, TX (US); Larry A. Jacobson, Richmond, TX (US); Daniel F. Dorffer, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 14/131,288

(22) PCT Filed: Jun. 18, 2012

(86) PCT No.: PCT/US2012/042869
§ 371 (c)(1),
(2), (4) Date: Jan. 7, 2014

(87) PCT Pub. No.: WO2013/012504
PCT Pub. Date: Jan. 24, 2013

(65) Prior Publication Data
US 2014/0142856 A1 May 22, 2014

Related U.S. Application Data

(60) Provisional application No. 61/509,935, filed on Jul. 20, 2011.

(51) Int. Cl.
*G01V 5/04* (2006.01)
*G01V 5/12* (2006.01)
(Continued)

(52) U.S. Cl.
CPC ............... *G01V 5/101* (2013.01); *G01N 33/24* (2013.01)
USPC .......................................... 702/8; 250/269.3

(58) Field of Classification Search
CPC ............. G01V 1/40; G01V 5/12; G01V 5/00; G01V 5/06; G01V 5/101; G01V 5/104; G01V 5/125; G06F 19/00; G01N 33/24; E21B 49/00
USPC ............. 702/6–8, 1–2, 11–13, 127–128, 179, 702/188–189; 73/152.06, 152.14, 152.42; 250/253, 269.1, 269.3–269.8
See application file for complete search history.

(56) References Cited

U.S. PATENT DOCUMENTS 3,993,902 A 11/1976 Neuman
4,020,342 A 4/1977 Smith, Jr. et al.
(Continued)

FOREIGN PATENT DOCUMENTS

GB 2427024 A 12/2006
WO 2007/015953 A2 2/2007
(Continued)

OTHER PUBLICATIONS

Albertin et al., The Many Facets of Pulsed Neutron Cased-Hole Logging, Summer 1996, Oilfield Review, pp. 28-41.*
(Continued)

*Primary Examiner* — Toan Le
(74) *Attorney, Agent, or Firm* — Chamberlain Hrdlicka

(57) ABSTRACT

Determining a value indicative of gas saturation of a formation. At least some of the illustrative embodiments are methods including: obtaining an inelastic count rate and a capture count rate of a gamma detector for a particular borehole depth; removing at least a portion of the chlorine response from the capture count rate, thereby creating a modified capture count rate; calculating a ratio of an inelastic count rate to the modified capture count rate for the particular borehole depth; determining a value indicative of gas saturation based on the ratio; and producing a plot of the value indicative of gas saturation as a function of borehole depth for a formation that the borehole at least partially penetrates.

23 Claims, 6 Drawing Sheets

(51) Int. Cl.
*G01V 5/10* (2006.01)
*G01N 33/24* (2006.01)

(56) References Cited

U.S. PATENT DOCUMENTS

| | | | | |
|---|---|---|---|---|
| 4,095,102 | A * | 6/1978 | Tixier | 250/265 |
| 4,122,339 | A | 10/1978 | Smith, Jr. et al. | |
| 4,631,405 | A | 12/1986 | Smith, Jr. | |
| 4,655,354 | A * | 4/1987 | Cohen | 211/199 |
| 5,528,030 | A | 6/1996 | Mickael | |
| 5,900,627 | A * | 5/1999 | Odom et al. | 250/269.7 |
| 6,005,244 | A | 12/1999 | Vaeth et al. | |
| 6,207,953 | B1 * | 3/2001 | Wilson | 250/269.4 |
| 7,117,092 | B2 | 10/2006 | Jacobson | |
| 7,361,887 | B2 | 4/2008 | Trcka et al. | |
| 7,365,308 | B2 | 4/2008 | Trcka et al. | |
| 7,372,018 | B2 | 5/2008 | Trcka et al. | |
| 7,511,266 | B1 * | 3/2009 | Bothner | 250/269.2 |
| 8,346,481 | B2 * | 1/2013 | Jacobson et al. | 702/8 |
| 2004/0133531 | A1 * | 7/2004 | Chen et al. | 706/8 |
| 2005/0121606 | A1 * | 6/2005 | Gilchrist et al. | 250/269.1 |
| 2006/0226351 | A1 | 10/2006 | Stoller et al. | |
| 2006/0243898 | A1 | 11/2006 | Gilchrist | |
| 2007/0023623 | A1 | 2/2007 | Trcka et al. | |
| 2007/0023624 | A1 | 2/2007 | Trcka et al. | |
| 2007/0023625 | A1 | 2/2007 | Trcka et al. | |
| 2007/0023626 | A1 | 2/2007 | Riley et al. | |
| 2010/0292927 | A1 | 11/2010 | Jacobson et al. | |
| 2011/0202276 | A1 * | 8/2011 | Truax et al. | 702/6 |

FOREIGN PATENT DOCUMENTS

| | | |
|---|---|---|
| WO | 2009/088651 A1 | 7/2009 |
| WO | 2010/123494 A1 | 10/2010 |
| WO | 2011-037583 A1 | 3/2011 |

OTHER PUBLICATIONS

Feng et al., Study on the Dual Gamma Spectrum Saturation Logging Method Based on Pulsed Neutron Source and Numerical Simulation, 2010, Chinese Journal of Geophysics, vol. 53, No. 5, pp. 892-900.*
PCT Search Report and Written Opinion, Application No. PCT/US12/042869, mailed Mar. 25, 2013.
Jacobson, L.A. et al., Response Characterization of an Induced Gamma Spectometry Tool Using a Bismuth Germanate Scintillator, The Log Analyst, Jul.-Aug. 1993, pp. 14-23.
Jacobson, L.A. et al., Intrinsic Capture Cross-Section and Porosity Transforms for the TMD-L Pulsed Neutron Capture Tool, SPE 30597, 1995, pp. 719-728.
Badruzzaman, A. et al. Progress and Future of Pulsed Neutron Technology in Oil Field Management, SPE 49228, 1998, pp. 1-15.
Badruzzaman, A. et al. Multi-Sensor Through-Casing Density and Saturation Measurement Concepts with a Pulsed Neutron Source: A Modeling Assessment, SPE 89884, 2004, pp. 1-14.
Badruzzaman, A. et al., Is Accurate Gas/Steam Determination Behind Pipe Feasible with Pulsed Neutron Measurements?, SPE 110098, 2007, pp. 1-18.
Odom, Richard et al. Design and Initial Field-Test Results of a New Pulsed-Neutron Logging System for Cased Reservoir Characterization, SPWLA 49th Annual Logging Symposium, May 25-28, 2008, pp. 1-9.
Jacobson, L.A. Elemental Yields and Complex Lithology Analysis From the Pulsed Spectral Gamma Log, The Log Analyst, Jan.-Feb. 1996, pp. 50-71.

* cited by examiner

US 8,996,315 B2

METHOD AND SYSTEM OF DETERMINING A VALUE INDICATIVE OF GAS SATURATION OF A FORMATION

CROSS-REFERENCE TO RELATED APPLICATIONS

None.

BACKGROUND

Well logging is a technique used to identify characteristics of earth formations surrounding a borehole. The interrogation of a formation surrounding a borehole to identify one or more characteristics may be by sound, electrical current, electromagnetic waves, or high energy nuclear particles (e.g., gamma particles and neutrons). Receiving the interrogating particle or signal, and determining a formation property from such particle or signal, is in many cases, a complicated endeavor sometimes involving detecting the interrogating particles or signals at multiple detectors on a logging tool. Any system or method that simplifies the detection of interrogating particle or signals, and thus simplifies determination of formation property, provides a competitive advantage in the marketplace.

BRIEF DESCRIPTION OF THE DRAWINGS

For a detailed description of exemplary embodiments, reference will now be made to the accompanying drawings in which:

FIG. 9 shows a computer system in accordance with at least some embodiments.

NOTATION AND NOMENCLATURE

Figure 1:
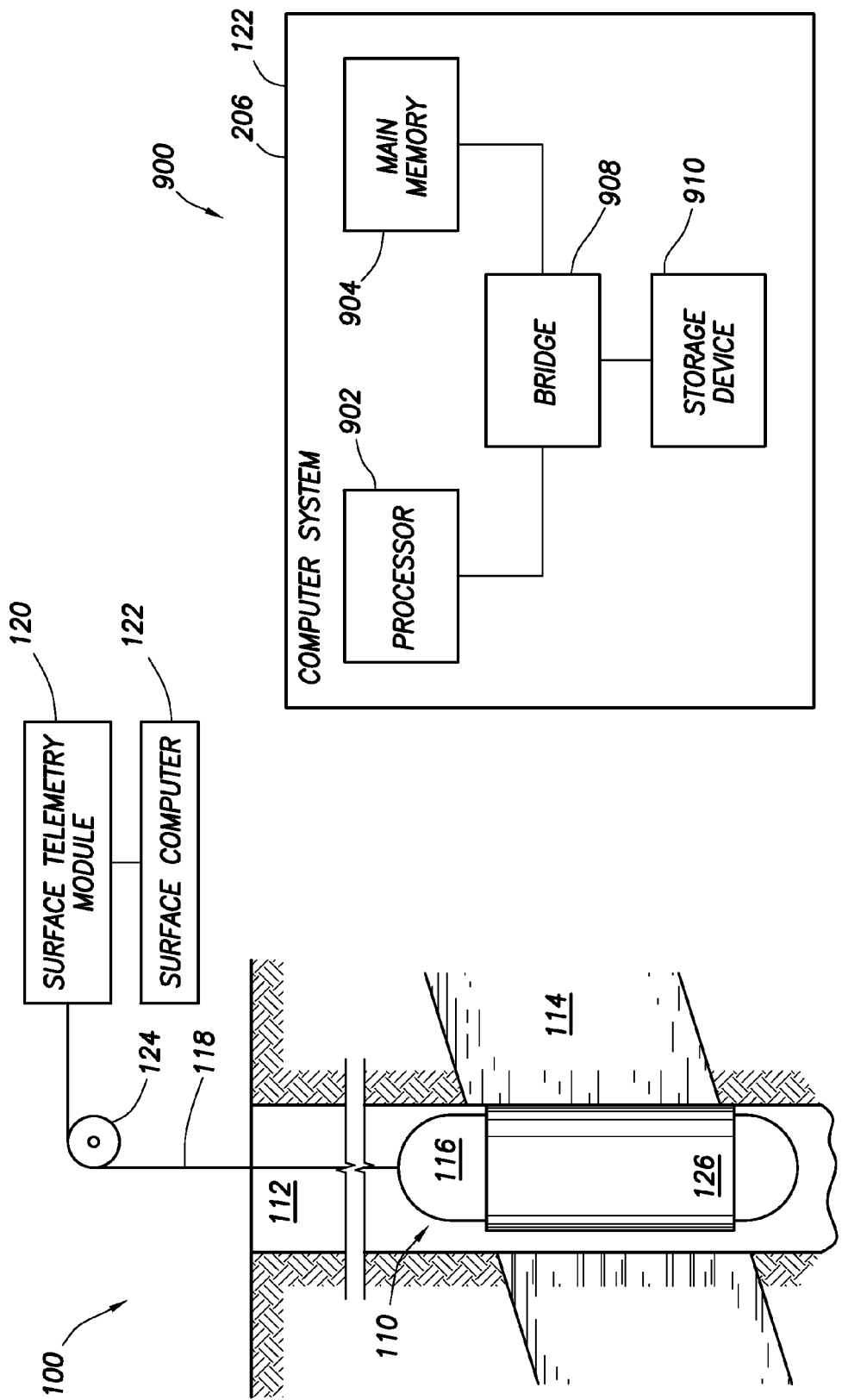
FIG. 1 shows a system in accordance with at least some embodiments.

Certain terms are used throughout the following description and claims to refer to particular system components. As one skilled in the art will appreciate, oilfield service companies may refer to a component by different names. This document does not intend to distinguish between components that differ in name but not function.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

"Gamma" or "gammas" shall mean energy created and/or released due to neutron interaction with atoms, and in particular atomic nuclei, and shall include such energy whether such energy is considered a particle (i.e., gamma particle) or a wave (i.e., gamma ray or wave).

"Gamma count rate decay curve" shall mean, for a particular gamma detector, a plurality of count values, each count value based on gammas counted during a particular time bin and/or having particular energy. The count values may be adjusted up or down to account for differences in the number of neutrons giving rise to the gammas or different tools, and such adjustment shall not negate the status as a "gamma count rate decay curve."

"Inelastic count rate" shall mean a gamma count rate during periods of time when gammas created by inelastic collisions are the predominant gammas created and/or counted (e.g., during the neutron burst period). The minority presence of counted capture gammas shall not obviate a count rate's status as an inelastic count rate.

"Capture count rate" shall mean a gamma count rate during periods of time when gammas created by thermal neutron capture are the predominant gammas created and/or counted (e.g., periods of time after the neutron burst period). The minority presence of counted inelastic gammas shall not obviate a count rate's status as capture count rate.

"Spacing", as between a neutron source and a gamma detector. shall mean a distance measured from a geometric center of the neutron source to a geometric center of a scintillation crystal of the gamma detector.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

The various embodiments were developed in the context of wireline logging tools, and thus the description that follows is based on the developmental context; however, the various systems and methods find application not only in wireline logging tools, but also measuring-while-drilling (MWD) and logging-while-drilling tools (LWD). Further still, the various embodiments also find application in "slickline" tools, in which the logging tool is placed downhole (e.g., as part of a drill string, or as a standalone device), and the logging tool gathers data that is stored in a memory within the device (i.e., not telemetered to the surface). Once the tool is brought back to the surface the data is downloaded, some or all the processing takes place, and the logging data is printed or otherwise displayed. Thus, the developmental context shall not be construed as a limitation as to the applicability of the various embodiments.

The various embodiments are directed to making determinations as to gas saturation (or oppositely stated, determinations as to water saturation) of underground formations based on a neutron-gamma tool. In particular, in situations where salinity of the water in an underground formation is not known, determining an accurate indication of gas saturation is difficult. The various embodiments address the issues, at least in part, by a system and method of determining a value indicative of gas saturation based on the gamma count rates from single gamma detector, where at least a portion of the response of chlorine in the capture count rates is removed. The specification first turns to an illustrative system.

FIG. 1 illustrates a nuclear logging system 100 constructed in accordance with at least some embodiments. In particular, system 100 comprises a logging tool 110 placed within a borehole 112 proximate to a formation 114 of interest. The tool 110 comprises a pressure vessel 116 within which various subsystems of the tool 110 reside, and in the illustrative case of FIG. 1 the pressure vessel 116 is suspended within the borehole 112 by a cable 118. Cable 118, in some embodiments a multi-conductor armored cable, not only provides support for the pressure vessel 116, but also in these embodiments communicatively couples the tool 110 to a surface telemetry module 120 and a surface computer 122. The tool a10 may be raised and lowered within the borehole 112 by way of the cable 118, and the depth of the tool 110 within the borehole 112 may be determined by depth measurement system 124 (illustrated as a depth wheel). In some embodiments, the pressure vessel 116 may be covered with a thermal neutron absorptive material 126 (the thickness of which is exaggerated for clarity of the figure); however, in other embodiments the material 126 may be only partially present or omitted altogether.

Figure 2:
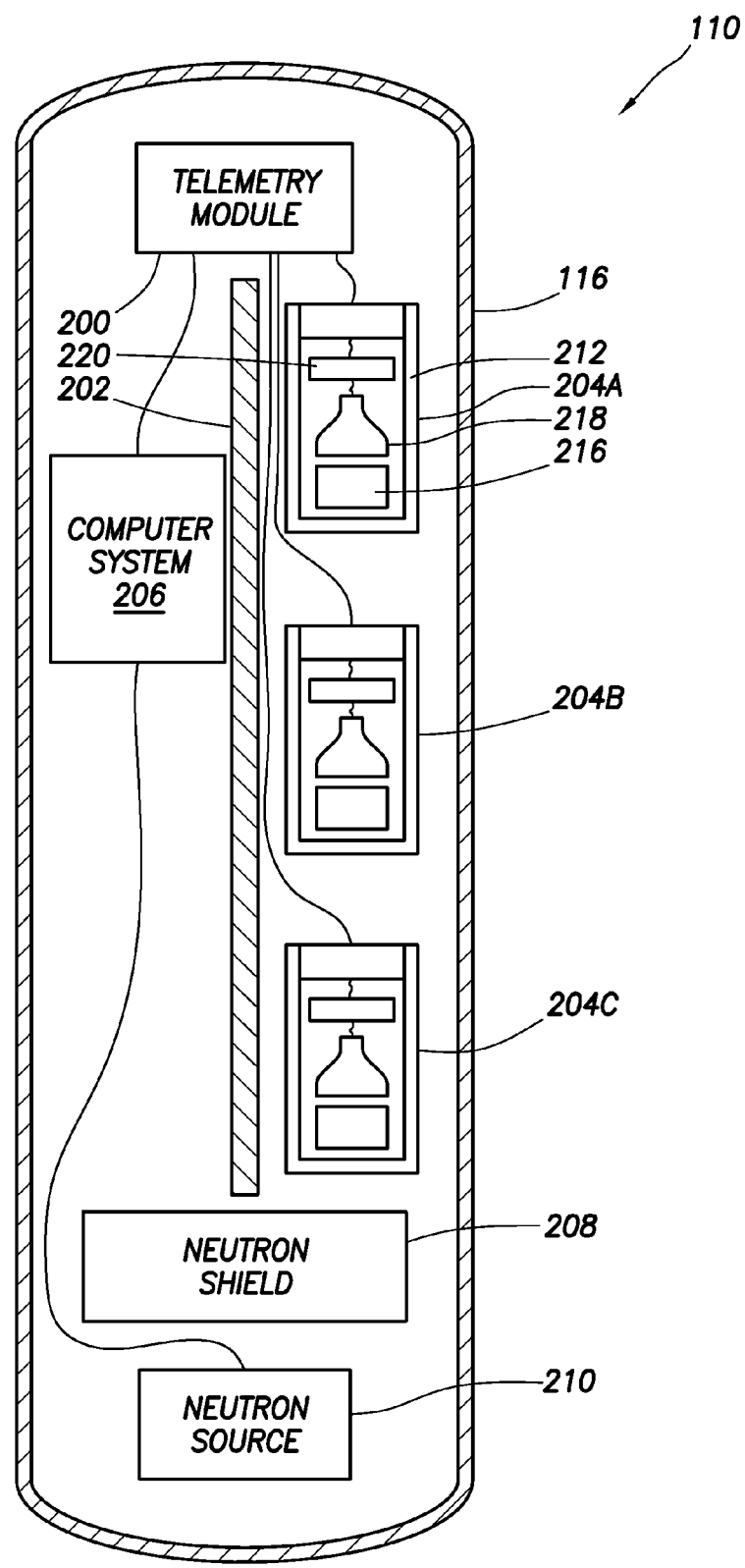
FIG. 2 shows a simplified cross-sectional view of a logging tool in accordance with at least some embodiments.

FIG. 2 shows a simplified cross-sectional view of the logging tool 110 to illustrate the internal components in accordance with at least some embodiments. In particular, FIG. 2 illustrates that the pressure vessel 116 houses various components, such as a telemetry module 200, borehole shield 202, a plurality of gamma detectors 204 (in this illustrative case three gamma detectors labeled 204A, 204B and 204C), computer system 206, a neutron shield 208 and a neutron source 210. While the gamma detectors 204 are shown above the neutron source 210, in other embodiments the gamma detectors may be below the neutron source. Gamma detector 204C may be on the order of 12 inches from the neutron source. The gamma detector 204B may be on the order of 24 inches from the neutron source 210. The gamma detector 204A may be on the order of 32.5 to 36 inches from the neutron source 210. Other spacing may be equivalently used. Neutron shield 202 may make the gamma detectors 204 more favorably receive formation-sourced gammas (as opposed to borehole-sourced gammas), and the shield may be a high density material (e.g., HEVIMET® available from General Electric Company of Fairfield, Conn.).

In some embodiments the neutron source 210 is a Deuterium/Tritium neutron generator. However, any neutron source capable of producing and/or releasing neutrons with sufficient energy (e.g., greater than 8 Mega-Electron Volt (MeV)) may equivalently used. The neutron source 210, under command from surface computer 122 in the case of wireline tools, or computer system 206 within the tool in the case of MWD, LWD or slickline tools, generates and/or releases energetic neutrons. In order to reduce the neutron exposure of the gamma detectors 204 and other devices by energetic neutrons from the neutron source 210, neutron shield 208 (e.g., HEVIMET®) separates the neutron source 210 from the gamma detectors 204. Because of the speed of the energetic neutrons (e.g., 30,000 kilometers/second or more), and because of collisions of the neutrons with atomic nuclei that change the direction of movement of the neutrons, a neutron flux is created around the logging tool 110 that extends into the formation 114.

Neutrons generated and/or released by the source 210 interact with atoms by way of inelastic collisions and/or thermal capture. In the case of inelastic collisions, a neutron inelastically collides with atomic nuclei, a gamma is created (an inelastic gamma), and the energy of the neutron is reduced. The neutron may have many inelastic collisions with the atomic nuclei, each time creating an inelastic gamma and losing energy. At least some of the gammas created by the inelastic collisions are incident upon the gamma detectors 204. One or both of the arrival time of a particular gamma and its energy may be used to determine status as an inelastic gamma.

After one or more inelastic collisions (and corresponding loss of energy) a neutron reaches an energy known as thermal energy (i.e., a thermal neutron). At thermal energy a neutron can be captured by atomic nuclei. In a capture event the capturing atomic nucleus enters an excited state, and the nucleus later transitions to a lower energy state by release of energy in the form of a gamma (known as a thermal gamma). At least some of the thermal gammas created by thermal capture are also incident upon the gamma detectors 204. One or both of the arrival time of a particular gamma and its energy may be used to determine its status as a capture gamma. Only inelastic and thermal capture interactions produce gammas, however.

Still referring to FIG. 2, when operational the gamma detectors 204 detect arrival and energy of gammas. Referring to gamma detector 204A as indicative of all the gamma detectors 204, a gamma detector comprises an enclosure 212, and within the enclosure 212 resides: a crystal 216 (e.g., yttrium/gadolinium silicate scintillation crystal or a bismuth germinate (BGO) scintillation crystal); a photo multiplier tube 218 in operational relationship to the crystal 216; and a processor 220 coupled to the photomultiplier tube 218. As gammas are incident upon/within the crystal 216, the gammas interact with the crystal 216 and flashes of light are emitted. Each flash of light itself is indicative of an arrival of a gamma, and the intensity of light is indicative of the energy of the gamma. The output of the photomultiplier tube 218 is proportional to the intensity of the light associated with each gamma arrival, and the processor 220 quantifies the output as gamma energy and relays the information to the surface computer 122 (FIG. 1) by way of the telemetry module 200 in the case of a wireline tool, or to the computer system 206 within the tool in the case of a MWD, LWD or slickline tools.

Figure 3:
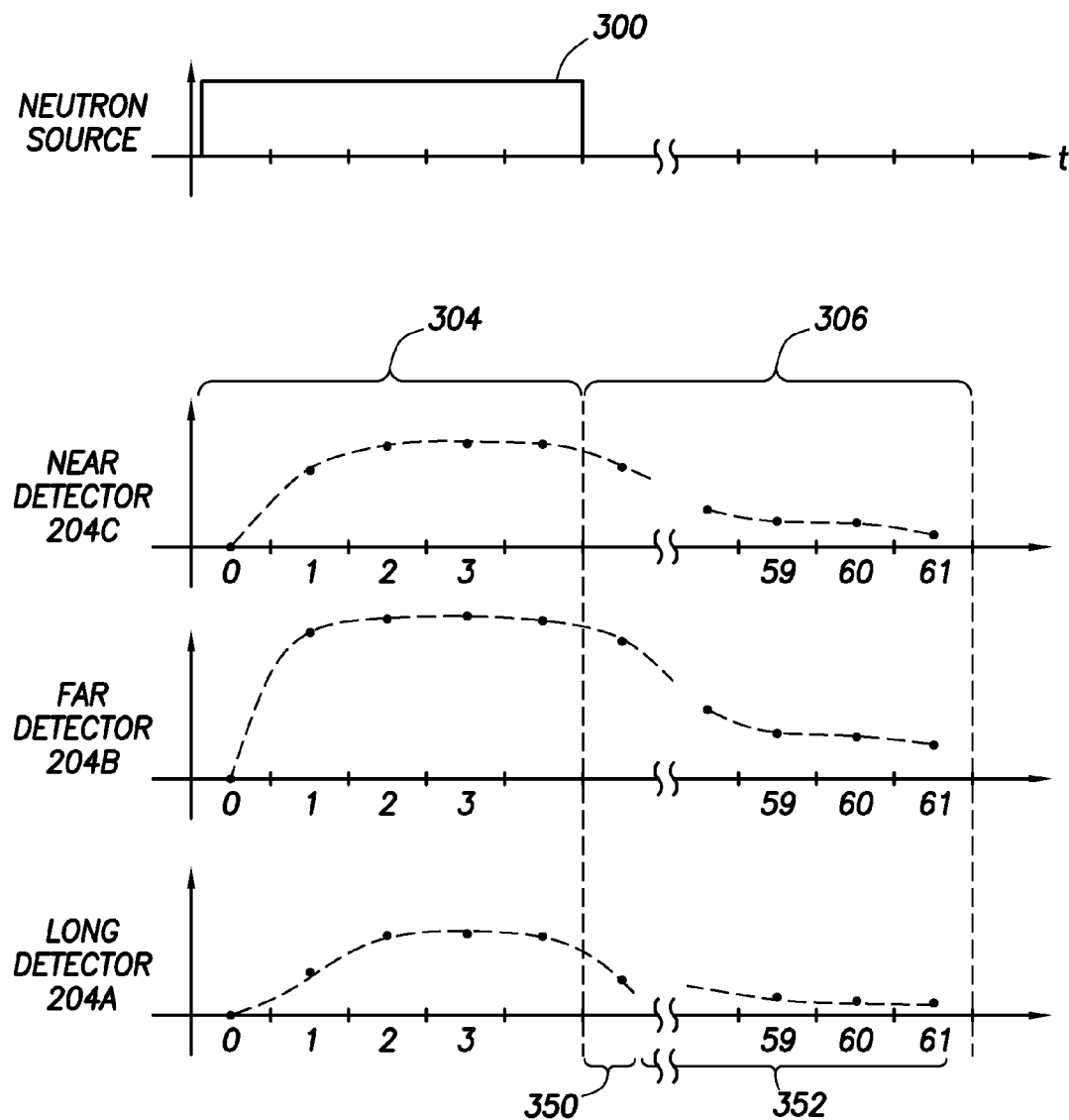
FIG. 3 shows a plurality of graphs of count rate as a function of time in accordance with at least some embodiments.

FIG. 3 shows a plurality of graphs as a function of corresponding time in order to describe how the gamma arrivals are recorded and characterized in accordance with at least some embodiments. In particular, FIG. 3 shows a graph relating to activation of the neutron source 210, as well as gamma count rates for the near detector 204C, the far detector 204B, and the long detector 204A. The graph with respect to the neutron source 210 is Boolean in the sense that it shows when the neutron source is generating and/or releasing neutrons (i.e., the burst period), and when the neutron source is not. In particular, with respect to the neutron source graph, the neutron source is generating and/or releasing neutrons during the asserted state 300, and the neutron source is off during the remaining time. In accordance with the various embodiments, a single interrogation (at a particular borehole depth) comprises activating the neutron source for a predetermined amount of time (e.g., 80 microseconds) and counting the number of gamma arrivals by at least one of the detectors during the activation time of the neutron source and for a predetermined amount of time after the source is turned off. In at least some embodiments, the total amount of time for a single interrogation (i.e., a single firing of the neutron source and the predetermined amount of time after the neutron source is turned off) may span approximately 1250 microseconds (µs), but other times may be equivalently used.

Still referring to FIG. 3, with respect to counting gamma arrivals by the gamma detectors 204, the interrogation time is divided into a plurality of time slots or time bins. With reference to the graph for the long detector 204A as illustrative of all the gamma detectors, in some embodiments the interrogation time is divided into 61 total time bins. In accordance with at least some embodiments, the first 32 time bins each span 10 µs, the next 16 time bins each span 20 µs, and the remaining time bins each span 50 µs. Other numbers of time bins, and different time bin lengths, may be equivalently used. Each gamma that arrives within a particular time bin increases the count value of gammas within that time bin. While in some embodiments the actual arrival time of the gammas within the time bin may be discarded, in other embodiments the actual arrival may be retained and used for other purposes. Starting with time bin 0, the gamma detector counts the gamma arrivals and increases the count value for the particular time bin for each gamma arrival. Once the time period for the time bin expires, the system starts counting anew the arrivals of gammas within the next time bin until count values for all illustrative 61 time bins have been obtained. In some cases, the system starts immediately again by activating the neutron source and counting further time bins; however, the count values within each time bin (for a particular borehole depth) are recorded either by way of the surface computer 122 in the case of wireline tools, or by the computer system 206 within the tool in the case of a MWD, LWD or slickline tools.

Illustrative count values for each time bin are shown in FIG. 3 as dots in the center of each time bin. The count value for each time bin is represented by the height of the dot above the x-axis (i.e., the y-axis value). Taking all the count values for a particular detector together, the dots may be connected by an imaginary line (shown in dashed form in FIG. 3) to form a mathematical curve illustrative of the number of gamma arrivals as a function of time detected by the particular gamma detector. In accordance with the various embodiments, the plurality of count values is referred to as a gamma count rate decay curve. All the curves taken together (the curve for each gamma detector) may be referred to as full-set decay curves.

Because of the physics of the combined logging tool and surrounding formation, within certain time periods certain types of gammas are more likely to be created, and thus more likely to be counted by the one or more active gamma detectors 204. For example, during the period of time within which the neutron source 210 is activated (as indicated by line 300), the energy of neutrons created and/or released leads predominantly to creation of inelastic gammas. The period of time in the gamma count rate decay curves where the gammas are predominantly inelastic gammas is illustrated by time period 304. Thus, gammas counted during some or all of the time period 304 may be considered inelastic gammas, and the count rate may be referred to as an inelastic count rate. Some capture gammas may be detected during the time period 304, and in some embodiments the minority presence of capture gammas may be ignored. In yet still other embodiments, because capture gammas are distinguishable from inelastic gammas based on energy, and because the gamma detectors not only detect arrival of a gamma but also energy, the portion of the count rate during time period 304 attributable to capture gammas may be removed algorithmically.

Similarly, after the neutron source 210 is no longer activated, the average energy of the neutrons that make up the neutron flux around the tool 110 decreases, and the lower energy of the neutrons leads predominantly to creation of capture gammas. The period of time in the gamma count rate decay curves where the gammas are predominantly capture gammas is illustrated by time period 306. Thus, gammas counted during some or all of the time period 306 may be considered capture gammas, and the count rate may be referred to as a capture count rate. Some inelastic gammas may be detected during the time period 306, and in some embodiments the minority presence of inelastic gammas may be ignored. In yet still other embodiments, because inelastic gammas are distinguishable from capture gammas based on energy, the portion of the count rate during time period 306 attributable to inelastic gammas may be removed algorithmically.

The inventors of the present specification have found that a count rate decay curve from a single gamma detector may be used to determine a value indicative of gas saturation of the formation 114 at the particular borehole depth for which the count rate decay curve is determined, even in the situation where salinity of the water in the formation is not known. More particularly still, the inventors of the present specification have found that a relationship between the inelastic count rate and the capture count rate of a gamma count rate decay curve is indicative of gas saturation, and that if the chlorine response from the capture count rate is removed an indication of gas saturation can be determined even in the absence of knowledge as to the salinity of water in the formation. Consider, as an example, a single gamma count rate decay curve, such as the long detector 204C gamma count rate decay curve of FIG. 3. In accordance with various embodiments, a ratio is taken of the inelastic count rate to a portion of capture count rate of the gamma count rate decay curve. The inelastic count rate may be the summed count rate from one or more of the time bins within time period 304. In accordance with some embodiments, the count rates from all the time bins within time period 304 are summed and used as the inelastic count rate. The capture count rate is based on the summed count rate from one or more of the time bins within time period 306. In accordance with some embodiments, portions of the count rates from time bins within time period 306 that span 100 µs to 1000 µs after the deactivation of the neutron source 210 may be used. In some embodiments, the ratio is the inelastic count rate divided by the portions of the capture count rate, and in other embodiments the ratio is portions of the capture count rate divided by the inelastic count rate. The specification now turns to various embodiments of selecting the portions of the capture count rate to be used.

Figure 4:
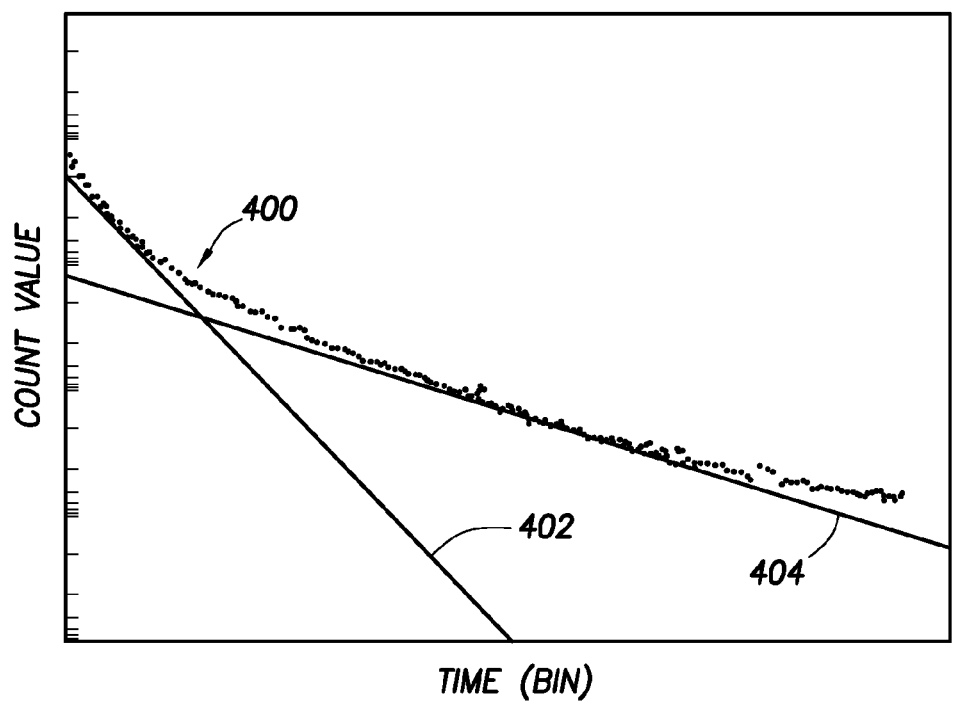
FIG. 4 shows a graph of capture count rates and sample curve fitting functions in accordance with at least some embodiments.

FIG. 4 shows a graph of an illustrative capture count rate decay curve. In particular, the X-axis of FIG. 4 is time (or bin number), and the Y-axis of FIG. 4 is count value (on a log scale). The line 400 formed by dots represent count values in each bin of the capture count rate (i.e., the count values within the time period 306). In accordance with these embodiments, the capture count rate decay curve may be thought of as comprising fast decay components (including a chlorine contribution) and slow decay components. Thus, in accordance with these embodiments the capture count rate represented by line 400 may be separated into fast decay components and the slow decay components. In particular, the illustrative line 400 can be approximated by two exponential functions. The straight line 402 represents the plotted solution of the exponential function with the faster decay time (i.e., the fast decay component). The straight line 404 represents the plotted solution of the exponential function with the slower decay time (i.e., the slow decay component). Lines 402 and 404 are shown in FIG. 4 as straight lines owing to the semi-log nature of the plot of FIG. 4. Stated otherwise, the capture gamma rate decay curve 400 may be approximated by the summation of the fast and slow decay components.

The exponential function associated with the fast decay components in these embodiments may take the form:

$$A_{fast}e^{tau1} \quad (1)$$

where $A_{fast}$ may be considered to be the total count rate under the line 402, e is the mathematical constant known as "Euler's number" and has a value of approximately 2.71828, and tau1 is proportional to decay time for the fast decay components. The exponential function associated with the slow decay components in these embodiments may take the form:

$$A_{slow}e^{tau2} \quad (2)$$

where $A_{slow}$ may be considered to be the total count rate under the line 404, e is the mathematical constant, and tau2 is proportional to decay time for the slow decay components.

Again, gammas based on chlorine interactions contribute most heavily to the fast decay components, and thus in these embodiments removing at least a portion of the chlorine response from the capture count rate involves discarding the fast decay component, and setting the modified capture count rate based on the slow decay components. More particularly still, in some embodiments a ratio is created based on the inelastic capture count rate and the capture count rate associated with the slow decay components, being $A_{slow}$ from the equation (2) above.

Figure 5:
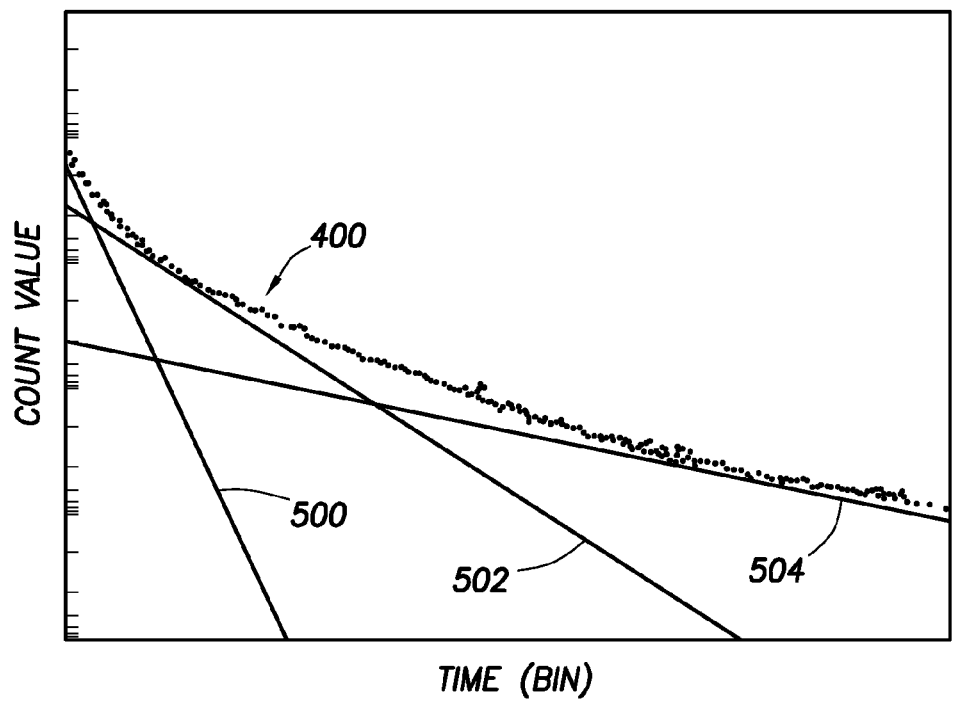
FIG. 5 shows a graph of capture count rates and sample curve fitting functions in accordance with at least some embodiments.

FIG. 4 illustrates separating the capture count rate into fast and slow decay components based on two functions (e.g., a first and second exponential function). FIG. 5, by contrast, shows a graph of an illustrative capture count rate decay curve where the X-axis is time (or bin number) and the Y-axis of is count value (on a log scale). The line 400 formed by dots represent again count values in each bin of the capture count rate (i.e., the count values within the time period 306). FIG. 5 additionally illustrates, however, that the capture count rate decay curve represented by line 400 may, in other embodiments, be approximated by two or more exponential functions, and as illustrated by three exponential functions. The straight line 500 represents the plotted solution of the exponential function with the fastest decay time, straight line 502 represents the plotted solution of the exponential function with the medium decay time, and straight line 504 represents the plotted solution of the exponential function with the slowest decay time (i.e., the slow decay component). As with respect to FIG. 4, lines 500, 502, and 504 are shown in FIG. 5 as straight lines owing to the semi-log nature of the plot. Again considering that chlorine contributes most heavily to the faster decay components, in these embodiments removing at least a portion of the chlorine response from the capture count rate involves discarding at least the fastest decay component and in some cases the medium decay components, and setting the modified capture count rate based on the slowest decay components. In other cases, both the medium decay components and slow decay components may be used.

In yet still further embodiments, rather than separating the capture count rate by curve fitting using two or more functions, the capture count rate decay curve illustrated in FIGS. 4 and 5 by line 400 may be curve fitted in-and-of itself. That is, through any of a variety of publically available software tools, the line 400 itself may be curve fitted against a logarithmic function. Once a function has been established that approximates the line 400, creating the ratio may involve using count rates attributable to only a portion of the single function to be the modified capture count rate. In particular, removing at least a portion of the chlorine response may comprise discarding counts attributable to portions of the function earlier in time in favor of counts attributable to portions of the function later in time. Thus, with a modified count value created based on only a portion of the single function, a ratio may be created with the inelastic count rate.

In yet still other embodiments, removing at least a portion of the chlorine response from the capture count rate may be based on discarding time bins in the early portion of the capture count rates (e.g., discarding time bins proximate in time to the end of the burst period of the neutron source). That is, inasmuch as chlorine contributes most heavily to the fast decay components in the capture count rate (i.e., the gammas that arrive at the beginning of the capture period), in yet still further embodiments the modified capture count rate may be based on a plurality of time bins proximate in time to the end capture period. For example (and referring briefly to FIG. 3), in these example embodiments the capture period may be divided into a time delay window 350 and sum window 352. The count values in bins within the time delay window 350 may be excluded from the capture count rate (e.g., time bins in the first 200 μs are excluded), and thus the capture count rate is based exclusively on count values within the sum window 352.

The various embodiments of removing at least a portion of the chlorine response from the capture count rates have been based on time-based arrivals of gammas in the capture period. However, gamma detectors in accordance with at least some embodiments also have the ability to determine energy of arriving gammas. In accordance with yet still further embodiments, removing at least a portion of the chlorine response may be performed in the energy domain. That is, one of the computer systems (e.g., surface computer 122 for wireline systems, or computer system 206 for LWD, MWD, and/or slickline tools) may identify gamma response of a plurality of elements within the capture count rate, one of the elements being chlorine. For example, the computer system may remove count values characteristic of the chlorine response to create the modified capture count rate. That is, the chlorine response may be gammas having a range of energies and corresponding range of counts for each energy; however, by spectral fitting the amount of each element present in the formation may be estimated, and then the count values attributable to chlorine may be removed. With the count values associated with chlorine removed, the ratio used to determine a value indicative of gas saturation may be based on the inelastic count rate and the modified capture count rate.

Figure 6:
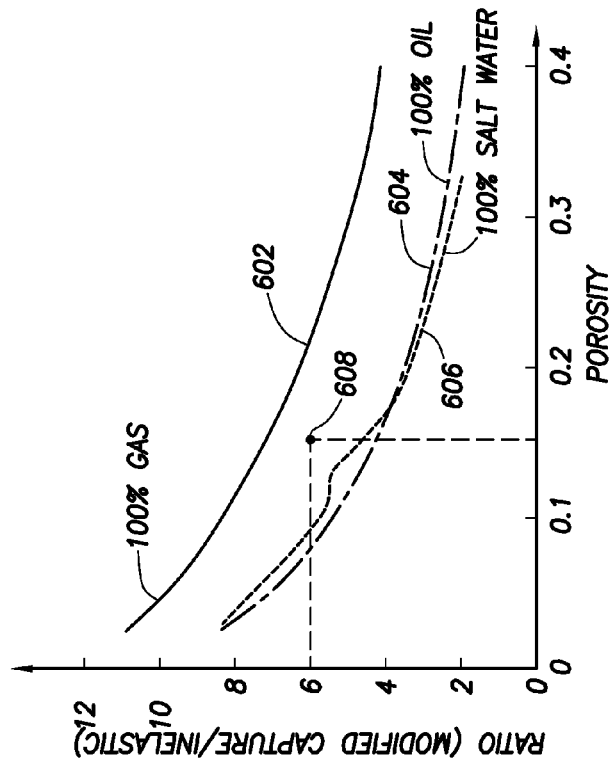
FIG. 6 shows an illustrative relationship between a ratio of inelastic count rate to modified capture count rate, porosity and gas saturation of a formation in accordance with at least some embodiments.

Regardless of the precise mechanism utilized to remove at least a portion of the chlorine response, using the ratio created based on the inelastic count rate and the modified capture count rate, a value of the gas saturation of the surrounding formation may be determined taking into account borehole size, drilling fluid type, casing size (if present), and porosity of the surrounding formation. FIG. 6 shows an illustrative relationship between a range of possible ratios (in the illustrative form of modified capture count rate divided by inelastic count rate), a range of possible porosities of the formation, and the gas saturation. The solid line 602 is representative of 100% gas saturation. The dash-dot-dash line 604 is representative of 100% oil saturation (0% gas). Likewise, the dashed line 606 is representative of 100% salt water saturation (again 0% gas). To a great extent, the lines 604 and 606 overlap in practice, but are separated slightly in the figure so as to be distinguishable. The relationship of FIG. 6 changes with changing borehole size, casing size, and borehole fluid type; however, such parameters will be known for each situation in which the logging tool is operated. The illustrative FIG. 6 is based on a 6-inch diameter borehole, a 4.5-inch diameter casing, and a hydrocarbon filled borehole.

A relationship such as that illustrated by FIG. 6 is used to determine a value indicative of gas saturation using the ratio of inelastic count rate to modified capture count rate and the porosity. If a plotted point (plotted based on a particular ratio at a particular porosity) falls on the 100% gas or 0% gas lines, then the value indicative of gas saturation is 100% or 0%, respectively for the particular ratio. If a plotted point falls between the 100% gas and 0% gas lines, the value indicative of gas saturation may be interpolated. In some cases, a straight line relationship may exist, such that a distance between the 100% gas and 0% gas lines directly indicates the value indicative of gas saturation. In other cases, the relationship may be other than a straight line relationship, in which case the value indicative of gas saturation may be determined based on the particular relationship. For the non-straight line case, the relationship may be determined (in advance in some embodiments) by any suitable method, such as modeling. In further embodiments, the gas saturation determined may be considered with a gas saturation value from a previous measurement of gas saturation at the particular borehole depth (e.g., after depletion caused by extraction and/or after a carbon dioxide injection procedure), and thus the value indicative of gas saturation may be a value of a change in gas saturation, such as gas depletion.

Consider, for purposes of explanation, that for a particular borehole depth a ratio value of approximately 6.0 is calculated, and that the porosity of the formation at the particular borehole depth is 0.15. Point 608 is representative of a ratio of 6.0 and porosity of 0.15. Plotted point 608 falls between 100% gas and 0% gas lines. Based on the relationship of the actual gas saturation when the ratio falls between the extremes, the value of indicative of gas saturation may be determined for the particular borehole depth based on the plotted point 608. The process of obtaining the gamma count rate decay curve, calculating the ratio, and determining the value indicative of gas saturation may be repeated for a plurality of borehole depths, and the values plotted. Plotting may be on chart paper with other formation parameters of interest, or the plotting may be by way of a computer monitor.

In order to test the discovery, and in particular to test the insensitivity to salinity, laboratory measurements were performed with a pulsed-neutron tool in a test borehole where the formations were 100% water saturated. The following table shows the results.

TABLE 1

| Formation | Formation Water | Porosity | ICR/CCR | ICR/MCCR |
|---|---|---|---|---|
| 22 pu Massilon Sand | Fresh | 22.13 | 1.77 | 1.17 |
| 33 pu Sand Pack | Fresh | 33.3 | 1.95 | 1.27 |
| 33 pu Sand Pack | Salt | 33.3 | 3.78 | 1.25 |

In particular, in the test borehole two formation types were present—Massilon sand and sand pack. Within the sand pack, two different types of water were present in different areas—fresh and salt water. Based on previous measurements, the porosity of each formation was known—22.13 for the Massilon sand and 33.3 for the sand pack. Using a pulse-neutron tool and the discovery above, a ratio of the inelastic count rate to capture count rate (i.e., un-modified) was made (ICR/CCR), as well as a ratio of the inelastic count rate to the modified capture count rate (ICR/MCCR). Notice how the ICR/MCCR ratio is substantially unaffected by the differences in salinity of the sand pack.

Figure 7:
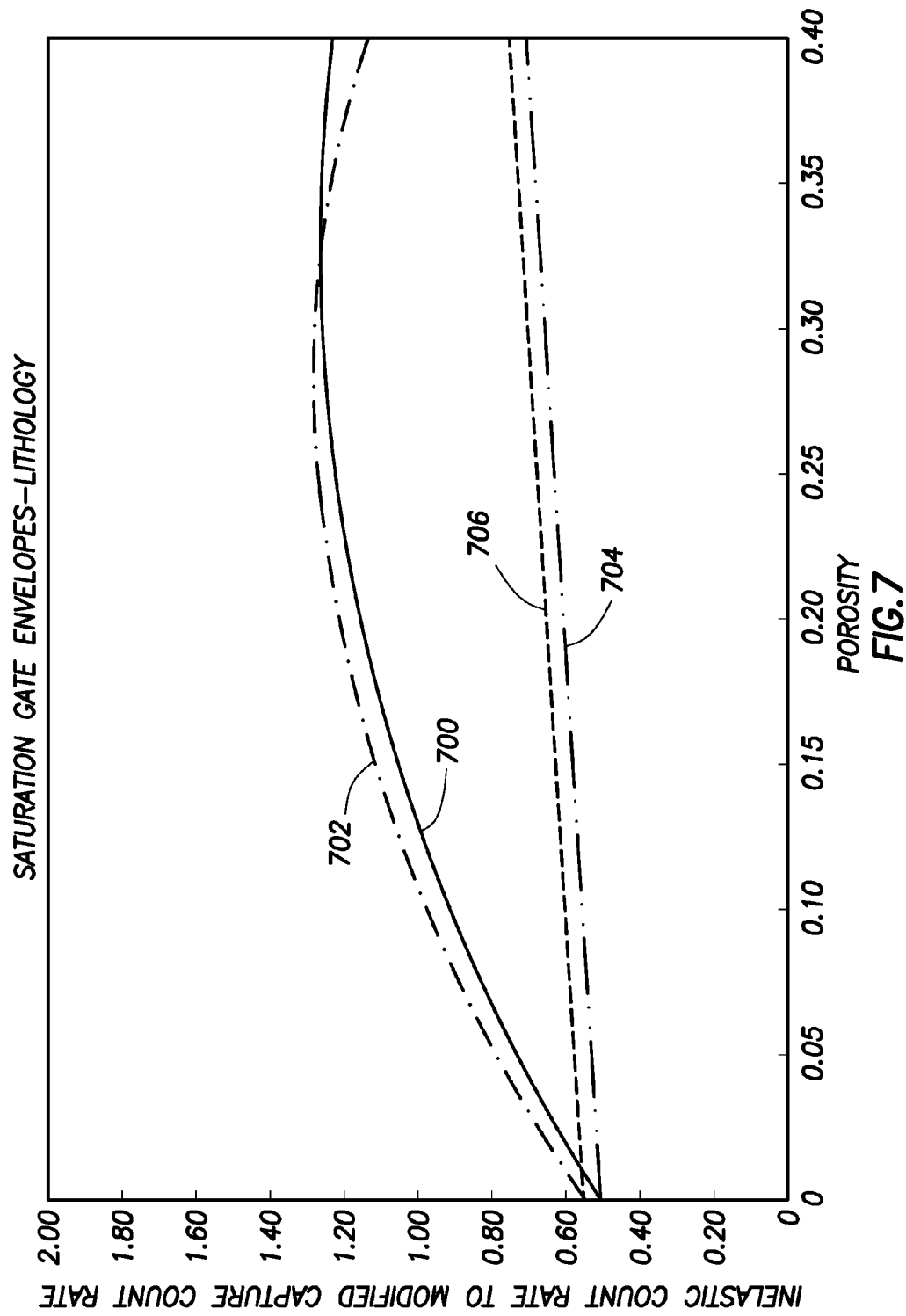
FIG. 7 shows a sample set of saturation gate envelopes with respect to lithology in accordance with at least some embodiments.

Moreover, in order to test application of the various embodiments against different lithology, a plurality of simulations was run, with the results illustrated by FIG. 7. In particular, FIG. 7 shows inelastic count range to modified capture count rate (Y-axis) against porosity (X-axis) for several formation types and saturation states. For example, solid line 700 shows a relationship between the illustrative ratio and porosity for 100% water saturation for a quartz formation. Dash-dot-dash line 702 shows a relationship between the illustrative ratio and porosity for a 100% water saturation for a calcite formation. While the two lines 700 and 702 show some separation so the lines will be distinguishable, in practice the separation is less than across the ration/porosity spectrum. On the gas side, dash-dot-dot-dash line 704 shows a relationship between the illustrative ratio and porosity for 100% gas saturation for a quartz formation. Dashed line 706 shows a relationship between the illustrative ratio and porosity for a 100% gas saturation for a calcite formation. While the two lines 704 and 706 show some separation so the lines will be distinguishable, in practice the separation is less than across the ration/porosity spectrum. The point is, the single detector method and system of determining an indication of gas saturation holds relatively constant across the different saturations spanning different formations.

The logging tool 110 of FIG. 2 illustrates three gamma detectors 204. However, in some embodiments of calculating the ratio and determining the value indicative of gas saturation utilizes the gamma count rate decay curves from a single gamma detector. In some cases, the long detector 204A provides better gamma count rate decay curves for determining the value indicative of gas saturation. However, as the porosity of the formation surrounding the borehole increases, better gamma count rate decay curves for determining the value indicative of gas saturation may be obtained from the closer spaced gamma detectors 204. Thus, in some embodiments, the gamma detector 204 used to read the gamma count rate decay curve for determination of the value indicative of gas saturation is selected based on a value indicative of porosity. For example, if the porosity of the formation is known prior to the running the tool 10 within the borehole (i.e., the porosity is determined non-contemporaneously with obtaining the gamma count rate decay curves and held in a database), then a gamma detector 204 may be selected based on the previously determined porosity. In yet still other embodiments, though only one gamma detector is needed for purposes of determining values indicative of gas saturation, two or more of the gamma detectors 204 may nevertheless be operational for measuring other formation parameters of interest, such as a value indicative of porosity. In embodiments where the value indicative of porosity (e.g., ratio of the capture count rate for two detectors) is measured contemporaneously with obtaining the gamma count rate decay curves, the gamma detector 204 used for determining the value indicative of gas saturation may be selected based on the contemporaneously determined value indicative of porosity. Further still, over the course of single logging run, multiple gamma detectors 204 may be used, one at a time, for determining the value indicative of gas saturation based on the values indicative of porosity of the formation at different borehole depths.

The various embodiments discussed to this point have implicitly assumed that the gamma count rate decay curves are obtained by a logging tool contemporaneously with calculating the ratio and determining the value indicative of gas saturation. However, in other embodiments calculating the ratio and determining the value indicative of gas saturation may take place non-contemporaneously with a logging tool obtaining the gamma count rate decay curves. Stated otherwise, the embodiments of determining a value indicative of the gas saturation may take place with respect to historical logging data gathered hours, days, weeks or months in advance of the calculating the ratio and determining the value indicative of gas saturation, so long as porosity values are also present, or can be calculated.

Figure 8:
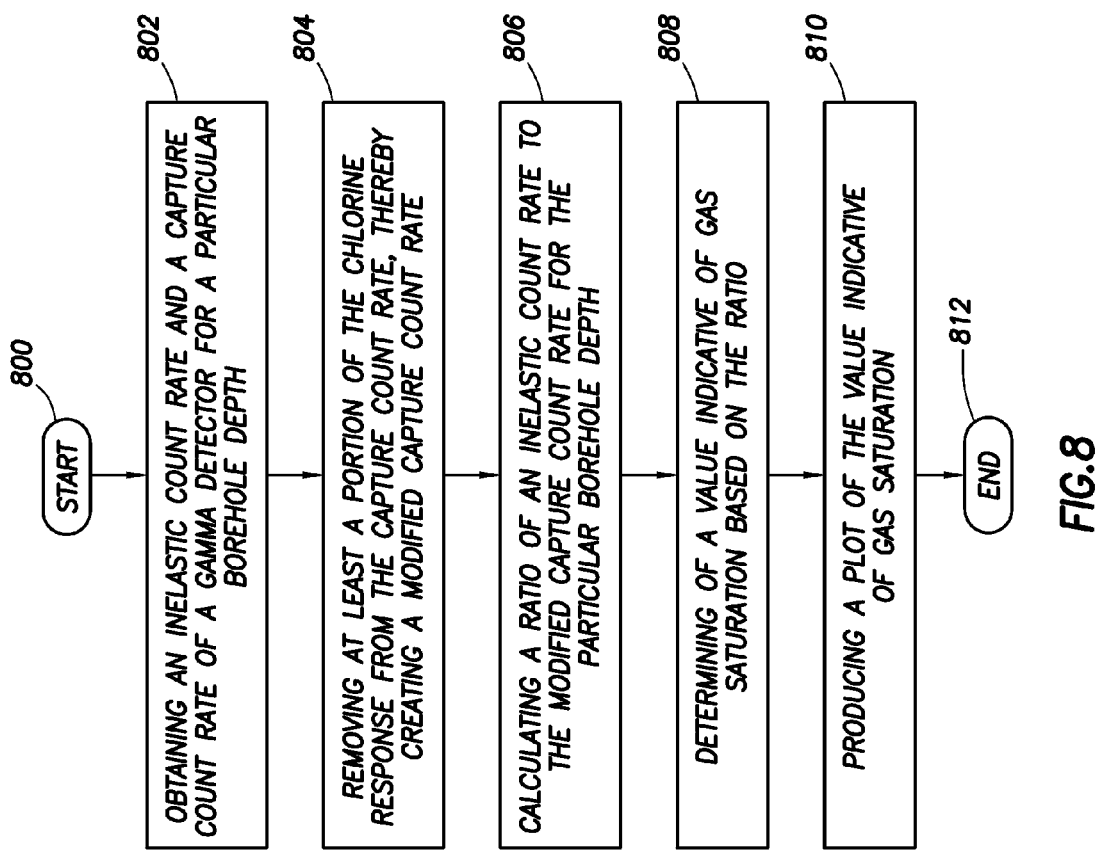
FIG. 8 shows a method in accordance with at least some embodiments.

FIG. 8 illustrates a method in accordance with at least some embodiments, where the method may be implemented, at least in part, by the surface computer system 122, the computer system 206 within the logging tool, or any other general purpose or special purpose computer system. In particular, the method starts (block 800) and proceeds to obtaining an inelastic count rate and a capture count rate of a gamma detector for a particular borehole depth (block 802). In some embodiments, the obtaining is by operation of the nuclear logging tool contemporaneously with the further steps of the illustrative method, while in other embodiments the obtaining is from a database of gamma count rates generated based on operation of the nuclear logging tool non-contemporaneously with the further steps of the illustrative method. Regardless of the precise mechanism of obtaining the gamma count rates, the illustrative method then moves to removing at least a portion of the chlorine response from the capture count rate, thereby creating a modified capture count rate (block 804). Any of a variety of methods, for example those discussed above, may be used to remove at least a portion of the chlorine response. Next, the illustrative method may comprise calculating a ratio of an inelastic count rate to the modified capture count rate for the particular borehole depth (block 806). In some embodiments the ratio is the inelastic count rate divided by the modified capture count rate, but in other embodiments the ratio is the modified capture count rate divided by the inelastic count rate. Next, the method moves to a determination of a value indicative of gas saturation based on the ratio (block 808). In some cases determination of the value may be based on porosity of the formation surrounding the borehole at the particular borehole depth, such as by a relationship similar to that shown in illustrative FIG. 6. While one value indicative of gas saturation at a particular borehole depth may be useful in some circumstances, in some cases the obtaining (block 802), calculating the ratio (block 806) and determining the value of gas saturation (block 808) may be repeated for a plurality of borehole depths. Thereafter, a plot of the value indicative of gas saturation is produced (block 810), and the illustrative method ends (block 812). The plotting may take many forms. In some cases, a paper plot with the value indicative of borehole depth may be created, and in yet other cases the plot may be by way of a display device coupled to a computer system.

FIG. 9 illustrates in greater detail a computer system 900, which is illustrative of both the surface computer system 122 and the computer system 206 within the logging tool 110. Thus, the computer system 900 described with respect to FIG. 9 could be proximate to the borehole during the time period within the tool 110 is within the borehole, the computer system 900 could be located at the central office of the oilfield services company, or the computer system 900 could be within the logging tool 110 (such as for LWD or MWD tools). The computer system 900 comprises a processor 902, and the processor couples to a main memory 904 by way of a bridge device 908. Moreover, the processor 902 may couple to a long term storage device 910 (e.g., a hard drive) by way of the bridge device 908. Programs executable by the processor 902 may be stored on the storage device 910, and accessed when needed by the processor 902. The program stored on the storage device 910 may comprise programs to implement the various embodiments of the present specification, including programs to implement selecting a gamma detector to use in the gas saturation determination, removing at least a portion of a chlorine response from a capture count rate, calculating the ratio of the inelastic gamma count rate to a modified capture gamma count rate, calculating the value of indicative of gas saturation, and producing a plot of the value indicative of gas saturation. In some cases, the programs are copied from the storage device 910 to the main memory 904, and the programs are executed from the main memory 904. Thus, both the main memory 904 and storage device 910 are considered computer-readable storage mediums. The ratios and values indicative of gas saturation predicted by the computer system 910 may be sent to a plotter that creates a paper-log, or the values may be sent to a display device which may make a representation of the log for viewing by a geologist or other person skilled in the art of interpreting such logs.

From the description provided herein, those skilled in the art are readily able to combine software created as described with appropriate general-purpose or special-purpose computer hardware to create a computer system and/or computer sub-components in accordance with the various embodiments, to create a computer system and/or computer sub-components for carrying out the methods of the various embodiments, and/or to create a non-transitory computer-readable storage medium (i.e., other than an signal traveling along a conductor or carrier wave) for storing a software program to implement the method aspects of the various embodiments.

References to "one embodiment," "an embodiment," "some embodiments," "particular embodiments", "various embodiments", or the like indicate that a particular element or characteristic is included in at least one embodiment of the invention. Although the phrases may appear in various places, the phrases do not necessarily refer to the same embodiment.

The above discussion is meant to be illustrative of the principles and various embodiments of the present invention. Numerous variations and modifications will become apparent to those skilled in the art once the above disclosure is fully appreciated. For example, in some embodiments, the counts associated with capture gammas are removed from the inelastic count rate, and counts associated with inelastic gammas are removed from the capture count rate, prior to calculating the ratio. In other cases, however, the presence of counts of capture gammas in the inelastic count rate, and likewise the presence of inelastic gammas in the capture count, is ignored for purposes of calculating the ratio. Finally, preprocessing of the data may take place, such as dead-time correction and environmental correction, without affecting scope of this specification. It is intended that the following claims be interpreted to embrace all such variations and modifications.

We claim:

1. A method comprising:
   obtaining, an inelastic count rate and a capture count rate of a gamma detector for a particular borehole depth;
   removing at least a portion of a chlorine response from the capture count rate, thereby creating a modified capture count rate;
   calculating a ratio of an inelastic count rate to the modified capture count rate for the particular borehole depth;
   determining a value indicative of gas saturation based on the ratio; and
   producing a plot of the value indicative of gas saturation as a function of borehole depth for a formation that the borehole at least partially penetrates.

2. The method of claim 1 wherein the step of removing at least a portion of the chlorine response from the capture count rate further comprises:

separating the capture count rate into at least two components being components exhibiting fast decay and components exhibiting slow decay; and
setting the modified capture count rate to be the components exhibiting slow decay.

3. The method of claim 1 wherein the step of removing at least a portion of the chlorine response from the capture count rate further comprises:
curve fitting the capture count rate to a first exponential function;
curve fitting the capture count rate to a second exponential function, the second exponential function having a longer time constant than the first exponential function; and
setting the modified capture count rate based on the second exponential function.

4. The method of claim 1 wherein the step of removing at least a portion of the chlorine response from the capture count rate further comprises:
curve fitting the capture count rate to a single function;
using only a portion of the single function to be the modified capture count rate.

5. The method of claim 1 wherein the step of removing at least a portion of the chlorine response from the capture count rate further comprises removing from the capture count rate count values in a plurality of time bins proximate in time to ending of a burst period of a neutron source.

6. The method of claim 1 wherein the step of removing at least a portion of the chlorine response from the capture count rate further comprises:
identifying response of a plurality of elements within the capture count rate; and
removing at least a portion a response attributable to chlorine from the capture count rate to create the modified capture count rate.

7. The method of claim 1 wherein the step of obtaining an inelastic count rate and a capture count rate of a gamma detector further comprises obtaining for a neutron source to gamma detector spacing of at least one selected from the group consisting of: greater than one foot; between one foot and five feet; between two feet and five feet.

8. The method of claim 1 wherein the step of obtaining an inelastic count rate and a capture count rate of a gamma detector further comprises obtaining from a database of count rates based on operation of a nuclear logging tool non-contemporaneously with the calculating.

9. A system comprising:
a downhole tool comprising a source of neutrons and a gamma detector, the gamma detector detects gamma arrivals;
a processor coupled to a memory, and the processor coupled to the gamma detector;
wherein the memory stores a program that, when executed by the processor, causes the processor to:
read an inelastic count rate from the gamma detector;
read a capture count rate from the gamma detector;
remove at least a portion of a chlorine response from the capture count rate to create a modified capture count rate;
calculate a ratio of inelastic count rate to the modified capture count rate of the gamma detector for a particular depth within a borehole; and
determine a value indicative of gas saturation for the particular depth based on the ratio.

10. The system of claim 9 wherein when the processor removes at least a portion of the chlorine response from the capture count rate to create a modified capture count rate, the program causes the processor to:
separate the capture count rate into at least components exhibiting fast decay and components exhibiting slow decay; and
set the modified capture count rate based on the components exhibiting slow decay.

11. The system of claim 9 wherein when the processor removes at least a portion of the chlorine response from the capture count rate to create a modified capture count rate, the program causes the processor to:
perform a curve fitting of the capture count rate to a first exponential function;
perform a curve fitting of the capture count rate to a second exponential function, the second exponential function having a longer time constant than the first exponential function; and
set the modified capture count rate based on the second exponential function.

12. The system of claim 9 wherein when the processor removes at least a portion of the chlorine response from the capture count rate to create a modified capture count rate, the program causes the processor to:
perform a curve fitting the capture count rate to a single function; and
set the modified capture count rate based on only a portion of the single function.

13. The system of claim 9 wherein when the processor removes at least a portion of the chlorine response from the capture count rate to create a modified capture count rate, the program causes the processor to remove capture count rate count values in a plurality of time bins proximate in time to ending of a burst period of a neutron source.

14. The system of claim 9 wherein when the processor removes at least a portion of the chlorine response from the capture count rate, the program causes the processor to:
identify response of a plurality of elements within the capture count rate; and
remove at least a portion a response attributable to chlorine from the capture count rate to create the modified capture count rate.

15. The system of claim 9 wherein the neutron source and gamma detectors spacing is selected from at least one of the group consisting of: greater than one foot; between one foot and five feet; between two feet and five feet.

16. The system of claim 9 wherein the processor is at least one selected from the group consisting of: a processor communicatively coupled to the downhole tool by way of a wireline; a processor that resides within the downhole tool.

17. A non-transitory computer-readable storage media storing a program that, when executed by a processor, causes the processor to:
obtain an inelastic count rate decay curve;
obtain a capture count rate decay curve;
remove at least a portion of a chlorine response from the capture count rate decay curve to create a modified capture count rate;
calculate a ratio of inelastic count rate to the modified capture count rate of the gamma detector for a particular depth within a borehole; and
determine a value indicative of gas saturation for the particular depth based on the ratio.

18. The non-transitory computer-readable storage media of claim 17 wherein when the processor removes at least a portion of the chlorine response from the capture count rate to create a modified capture count rate, the program causes the processor to:

separate the capture count rate into at least components exhibiting fast decay and components exhibiting slow decay; and set the modified capture count rate based on the components exhibiting slow decay.

19. The non-transitory computer-readable storage media of claim 17 wherein when the processor removes at least a portion of the chlorine response from the capture count rate to create a modified capture count rate, the program causes the processor to:

perform a curve fitting of the capture count rate to a first exponential function;

perform a curve fitting of the capture count rate to a second exponential function, the second exponential function having a longer time constant than the first exponential function; and set the modified capture count rate based on the second exponential function.

20. The non-transitory computer-readable storage media of claim 17 wherein when the processor removes at least a portion of the chlorine response from the capture count rate to create a modified capture rate, the program\causes the processor to:

perform curve fitting the capture count rate to a single function; and set the modified capture count rate based on only a portion of the single function.

21. The non-transitory computer-readable storage media of claim 17 wherein when the processor removes at least a portion of the chlorine response from the capture count rate to create a modified capture count rate, the program causes the processor to remove capture count rate count values in a plurality of time bins proximate in time to ending of a burst period of a neutron source.

22. The non-transitory computer-readable storage media of claim 17 wherein when the processor removes at least a portion of the chlorine response from the capture count rate to create a modified capture count rate, the program causes the processor to:

identify a response of a plurality of elements within the capture count rate; and remove at least a portion a response attributable to chlorine from the capture count rate to create the modified capture count rate.

23. The non-transitory computer-readable storage media of claim 17 wherein when the processor obtains an inelastic count rate and capture count rate decay curve, the program causes the processor to obtain the count rates from a repository of count rates based on operation of the nuclear logging tool non-contemporaneously with the calculating.

* * * * *